US006710207B2

(12) United States Patent
Bogan, Jr. et al.

(10) Patent No.: US 6,710,207 B2
(45) Date of Patent: Mar. 23, 2004

(54) METHODS FOR PRODUCING UNSATURATED CARBOXYLIC ACIDS AND UNSATURATED NITRILES

(75) Inventors: Leonard Edward Bogan, Jr., Hatfield, PA (US); Scott Han, Lawrenceville, NJ (US); Bradley Anson Jacobs, Chalfont, PA (US); Frederick William Kaiser, Fort Washington, PA (US); Peter David Klugherz, Huntingdon Valley, PA (US); Manhua Lin, Levittown, PA (US); Richard David Link, III., Levittown, PA (US); Michael William Linsen, North Wales, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/962,487

(22) Filed: Sep. 25, 2001

(65) Prior Publication Data
US 2003/0187297 A1 Oct. 2, 2003
(Under 37 CFR 1.47)

Related U.S. Application Data

(60) Provisional application No. 60/236,031, filed on Sep. 28, 2000.

(51) Int. Cl.$^7$ .......................... C07C 51/16; B01J 23/22
(52) U.S. Cl. ..................... 562/549; 502/312; 502/311
(58) Field of Search .................. 562/549; 502/312, 502/311

(56) References Cited

U.S. PATENT DOCUMENTS

| 5,049,692 A | 9/1991 | Hatano et al. |
| 5,281,745 A | 1/1994 | Ushikubo et al. |
| 5,380,933 A | 1/1995 | Ushikubo et al. |
| 5,430,209 A | 7/1995 | Agaskar et al. |
| 5,430,210 A | 7/1995 | Grasselli et al. |
| 5,532,384 A | 7/1996 | Shirley et al. |
| 5,705,684 A | 1/1998 | Hefner et al. |
| 5,726,327 A | 3/1998 | Acharya et al. |
| 5,994,580 A | 11/1999 | Takahashi et al. |

FOREIGN PATENT DOCUMENTS

| EP | 0 484 136 B1 | 5/1992 |
| EP | 0 495 504 B1 | 7/1992 |
| EP | 0 585 023 A1 | 3/1994 |
| EP | 0 608 838 | 8/1994 |
| EP | 0 961 253 A2 | 12/1999 |
| JP | 7-53448 | 2/1995 |
| WO | WO 97/36849 | 10/1997 |
| WO | WO 00/09260 | 2/2000 |
| WO | WO 00/29105 | 5/2000 |
| WO | WO 00/29106 | 5/2000 |

OTHER PUBLICATIONS

Translation of Japanese Laid–Open Patent Application Publication No. 6–228073 (Aug. 16, 1994).

Abstract of Soviet Union Patent No. 745903 (Jul. 7, 1980).

Primary Examiner—Joseph K. McKane
Assistant Examiner—Golam M M Shameem

(57) ABSTRACT

Unsaturated carboxylic acids are produced by the vapor phase catalytic oxidation of mixtures of alkenes and alkanes in the presence of a catalyst containing a mixed metal oxide. Similarly, unsaturated nitrites are produced by the vapor phase catalytic oxidation of alkenes or mixtures of alkenes and alkanes and ammonia in the presence of a catalyst containing a mixed metal oxide.

9 Claims, No Drawings

METHODS FOR PRODUCING UNSATURATED CARBOXYLIC ACIDS AND UNSATURATED NITRILES

CROSS REFERENCE TO RELATED PATENT APPLICATIONS

This is a non-provisional application of prior U.S. provisional applications Ser. No. 60/236,031 filed on Sep. 28, 2000 now abandoned.

The present invention relates to a method for producing unsaturated carboxylic acids by subjecting a mixture of alkene(s) and alkane(s) to vapor phase catalytic oxidation. More particularly, the present invention relates to a method suitable for producing acrylic acid or methacrylic acid by vapor phase catalytic oxidation of a mixture of propene and propane, or a mixture of isobutene and isobutane, respectively.

The present invention also relates to a method of producing unsaturated nitriles by subjecting alkene(s) or a mixture of alkene(s) and alkane(s) to vapor phase catalytic oxidation in the presence of ammonia. More particularly, the present invention relates to a method suitable for producing acrylonitrile or methacrylonitrile by vapor phase catalytic oxidation, in the presence of ammonia, of propene or a mixture of propene and propane, or isobutene or a mixture of isobutene and isobutane, respectively.

Nitriles, such as acrylonitrile and methacrylonitrile, have been industrially produced as important intermediates for the preparation of fibers, synthetic resins, synthetic rubbers, and the like. The most popular method for producing such nitriles is to subject an olefin such as propene or isobutene to a catalytic reaction with ammonia and oxygen in the presence of a catalyst in a gaseous phase at a high temperature. Known catalysts for conducting this reaction include a Mo—Bi—P—O catalyst, a V—Sb—O catalyst, an Sb—U—V—Ni—O catalyst, a Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by the ammoxidation reaction wherein a lower alkane, such as propane or isobutane, is used as starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula $$Mo_aV_bTe_cX_xO_n$$

wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles(±0.3°) of 2θ in its X-ray diffraction pattern: 22.1°, 28.2°, 36.2°, 45.2° and 50.0°.

There is no disclosure, whatsoever, of the use of alkenes in the feed and only a propane feed is cited in the examples.

Similarly, Japanese Laid-Open Patent Application No. 6-228073 discloses a method of nitrile preparation comprising reacting an alkane in a gas phase contact reaction with ammonia in the presence of a mixed metal oxide catalyst of the formula $$W_aV_bTe_cX_xO_n$$

wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium and, when a=1, b=0.01 to 1.0, c=0.01 to 1.0, x=0.01 to 1.0 and n is determined by the oxide form of the elements.

There is no disclosure, whatsoever, of the use of alkenes in the feed and only a propane feed is cited in the examples.

The ability to convert alkene(s) or a mixed feed of alkene(s) and alkane(s) to the corresponding unsaturated nitrile with a mixed metal oxide catalyst is believed to be novel in that it could not be anticipated that a mixed metal oxides which ammoxidizes alkanes to the corresponding unsaturated nitrile would necessarily also oxidize alkenes to the same product.

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but, the technology is well established.

It is also known to produce acrylic acid by oxidation of propene in the presence of a mixed metal oxide catalyst.

Japanese Laid-Open Patent Application No. 07-053448 discloses the preparation of acrylic acid by the gas-phase catalytic oxidation of propene in the presence of a mixed metal oxide catalyst of the formula $$Mo_aV_bTe_cX_dO_n$$

wherein X is at least one element selected from Nb, Ta, W, Ti, Al, Zr, Cr, Mn, Fe, Ru, Co, Rh, Ni, Pd, Pt, Sb, Bi, B, In, Li, Na, K, Rb, Cs and Ce; a=0.25–0.98; b=0.003–0.5; c=0.003–0.5; d=0.003–0.5 and n is determined by the oxidation state of the other elements.

Similarly, Published International Application No. WO 2000/09260 discloses a catalyst for the selective oxidation of propene to acrylic acid and acrolein which comprises a mixed metal oxide of molybdenum, vanadium, lanthanum, palladium, niobium, and copper and/or chromium wherein the metals are present in the ratios given by the formula $$Mo_aV_bLa_cPd_dNb_eX_f$$

wherein X=Cu and/or Cr; a=1; b=0.01 to 0.9; c=greater than zero to 0.22; d=0.0000001 to 0.2; e=0 to 0.2; and f=0 to 0.2.

U.S. Pat. No. 5,994,580 discloses the recycle of by-product propene in a process for producing acrylic acid from propane and oxygen gas through a vapor-phase catalytic oxidation reaction, the process comprising conducting the reaction using as a catalyst a metal oxide containing the metallic elements Mo, V, Sb and A (wherein A is at least one of Nb, Ta, Sn, W, Ti, Ni, Fe, Cr and Co), the metal oxide having been prepared by a process including specific steps (1) and (2). Step (1) comprises reacting $V^{+5}$ with $Sb^{+3}$ in an aqueous medium at a temperature of 70° C. or more in the presence of $Mo^{+6}$ and, during or after the reaction, bubbling either molecular oxygen or a gas containing molecular oxygen into the reaction mixture. Step (2) comprises adding a compound containing the element A as a component thereof to the reaction product obtained in step (1), mixing the ingredients to obtain a homogeneous mixture, and burning the resulting mixture.

Commercial incentives exist for producing acrylic acid using a lower cost propane feed. Therefore, the prior art describes cases wherein a mixed metal oxide catalyst is used to convert propane to acrylic acid in one step.

In particular, U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components exclusive of oxygen, satisfy the following relationships: 0.25<r(Mo)<0.98, 0.003<r(V)<0.5, 0.003<r(Te)<0.5 and 0.003<r(X)<0.5, wherein r(Mo), r(V), r(Te) and r(X) are the molar fractions of Mo, V, Te and X, respectively, based on the total amount of the essential components exclusive of oxygen.

The patent discusses various potential gas feed variations for use with the mixed metal oxide catalyst. In particular, there are disclosed the use of $C_{3-8}$alkanes, oxygen (possibly in the form of air), steam and possibly an inert component such as nitrogen, argon or helium. There is no disclosure, whatsoever, of the use of alkenes in the feed and only alkane feeds are cited in the examples. More particularly, as noted at col. 5, lines 27–32, of the patent: "The purity of the starting material alkane is not particularly limited, and an alkane containing a lower alkane such as methane or ethane, air or carbon dioxide, as impurities, may be used without any particular problem. Further, the starting material alkane may be a mixture of various alkanes."

The ability to convert a mixed feed of alkene(s) and alkane(s) to the corresponding unsaturated carboxylic acid is believed to be novel in that it could not be anticipated that a mixed metal oxide which oxidizes alkane(s) to the corresponding unsaturated carboxylic acid would necessarily oxidize alkene(s) to the same product. For example, substituting propane for propene as a feed to a commercial propene to acrylic acid process gives zero propane conversion with no partial oxidation products. Also in the prior art, U.S. Pat. No. 5,705,684 discloses a process where propane is converted to propene by an oxidative dehydrogenation first step (called "Stage A") resulting in a mixed propane/propene feed for further oxidation to acrolein and acrylic acid (called "Stage B"). The patent notes, at col. 5, lines 45–49, that ". . . the oxidation Stage B is fed with a feed gas mixture consisting essentially of only propylene, molecular oxygen and propane. The latter constituent is essentially the inert diluent gas, while the first two are the reactants." Similarly, even if the catalyst were active to convert either an alkene or an alkane to a desired product, it would not be expected that the same reaction conditions would prevail for both reactants, since the alkene, by virtue of its unsaturation, would be believed to be more active than the alkane, lacking such a site.

In the present invention, the alkene is a key feed component. Advantageous results from using a mixed feed of alkene and alkane include higher yields and potentially less severe operating conditions. In addition, the availability of mixed alkane/alkene feeds from sources is often improved and may include price incentives (e.g., lower separation costs) relative to using the pure alkane feeds described in the aforementioned U.S. Pat. No. 5,380,933. The processes of the present invention are able to utilize a mixture of alkene and alkane. With both the alkene and the alkane present, the processes of the present invention are able to utilize the combined feed and convert both alkane and alkene to the desired product without the penalty of one of those components being an extra inert feed diluent.

Thus, in a first aspect, the present invention provides, a method for producing an unsaturated carboxylic acid, which comprises subjecting a mixture of an alkene and an alkane, containing at least 0.5% by weight of said alkene, to a single-pass vapor phase catalytic oxidation reaction in the presence of a catalyst containing a mixed metal oxide having the formula

$$A_aM_mN_nX_xO_o$$

wherein A is at least one element selected from the group consisting of molybdenum and tungsten, M is at least one element selected from the group consisting of vanadium and cerium, N is at least one element selected from the group consisting of tellurium and selenium, and X is at least one element selected from the group consisting of niobium, tantalum, titanium, aluminum, zirconium, chromium, manganese, iron, ruthenium, cobalt, rhodium, nickel, platinum, antimony, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium; and
wherein when a=1, m=0.01 to 1.0, n=0.01 to 1.0, x=0.01 to 1.0 and o is dependent on the oxidation state of the other elements.

In a second aspect, the present invention provides a method for producing an unsaturated nitrile, which comprises subjecting a mixture of an alkene, or a mixture of an alkene and an alkane, containing at least 0.5% by weight of said alkene, and ammonia to a vapor phase catalytic oxidation reaction in the presence of a catalyst containing a mixed metal oxide having the formula

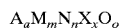
$$A_aM_mN_nX_xO_o$$

wherein A is at least one element selected from the group consisting of molybdenum and tungsten, M is at least one element selected from the group consisting of vanadium and cerium, N is at least one element selected from the group consisting of tellurium, antimony and selenium, and X is at least one element selected from the group consisting of niobium, tantalum, titanium, aluminum, zirconium, chromium, manganese, iron, ruthenium, cobalt, rhodium, nickel, platinum, antimony, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium; and wherein when a=1, m=0.01 to 1.0, n=0.01 to 1.0, x=0.01 to 1.0 and o is dependent on the oxidation state of the other elements.

The mixed metal oxide to be used as a catalyst component of the first aspect of the present invention has the formula $A_a M_m N_n X_x O_o$ wherein A is at least one element selected from the group consisting of molybdenum and tungsten, M is at least one element selected from the group consisting of vanadium and cerium, preferably vanadium, N is at least one element selected from the group consisting of tellurium and selenium, preferably tellurium, and X is at least one element selected from the group consisting of niobium, tantalum, titanium, aluminum, zirconium, chromium, manganese, iron, ruthenium, cobalt, rhodium, nickel, platinum, antimony, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium, preferably niobium, tantalum and zirconium, most preferably niobium.

The mixed metal oxide to be used as a catalyst component of the second aspect of the present invention has the formula $A_a M_m N_n X_x O_o$ wherein A is at least one element selected from the group consisting of molybdenum and tungsten, M is at least one element selected from the group consisting of vanadium and cerium, preferably vanadium, N is at least one element selected from the group consisting of tellurium, antimony and selenium, preferably tellurium and/or antimony, most preferably tellurium, and X is at least one element selected from the group consisting of niobium, tantalum, titanium, aluminum, zirconium, chromium, manganese, iron, ruthenium, cobalt, rhodium, nickel, platinum, antimony, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium, preferably niobium, tantalum and zirconium, most preferably niobium.

The proportions of the respective components of the above-noted catalysts, based on the total amount of the components, are within the ranges defined by the following relationship: when a=1, m=0.01 to 1.0, n=0.01 to 1.0, x=0.01 to 1.0 and o is dependent on the oxidation state of the other elements. The ranges represented by the following relationship are particularly preferred: when a=1, m=0.2 to 0.4, n=0.2 to 0.4 and x=0.01 to 0.2. The value of o, i.e. the amount of oxygen present, is dependent on the oxidation state of the other elements in the catalyst. However, o is typically in the range of from 3 to 4.7.

Particularly preferred mixed metal oxides have the formulae $Mo_a V_m Te_n Nb_x O_o$ and $W_a V_m Te_n Nb_x O_o$ wherein a, m, n, x and o are as previously defined.

Further, as the mixed metal oxide, one having a certain specific crystal structure is preferred. Specifically, preference is given to the one which exhibits the following five main diffraction peaks at specific diffraction angles 2θ in the X-ray diffraction pattern of the mixed metal oxide (as measured using Cu—Kα radiation as the source):

| X-ray lattice plane | | |
| --- | --- | --- |
| Diffraction angle 2θ (±0.30) | Spacing medium (Å) | Relative intensity |
| 22.1° | 4.02 | 100 |
| 28.2° | 3.16 | 20~450 |
| 36.2° | 2.48 | 5~60 |
| 45.2° | 2.00 | 2~40 |
| 50.0° | 1.82 | 2~40 |

The intensity of the X-ray diffraction peak may vary depending upon the measuring conditions of each crystal. However, the intensity relative to the peak intensity at 22.1° being 100, is usually within the above ranges. Generally, the peak intensities at 2θ = 22.1° and 28.2° are distinctly observed. However, so long as the above five diffraction peaks are observable, the basic crystal structure is the same even if other peaks are observed in addition to the five diffraction peaks, and such a structure is useful for the present invention.

The intensity of the X-ray diffraction peak may vary depending upon the measuring conditions of each crystal. However, the intensity relative to the peak intensity at 22.1° being 100, is usually with the above ranges. Generally, the peak intensities at 2θ=22.1° and 28.2° are distinctly observed. However, so long as the above five diffraction peaks are observable, the basic crystal structure is the same even if other peaks are observed in addition to the five diffraction peaks, and such a structure is useful for the present invention.

The mixed metal oxides of the present invention may be prepared in the following manner.

In a first step, a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain elements A, M, N, O and X, as previously defined.

Suitable solvents include water, alcohols including, but not limited to, methanol, ethanol, propanol, and diols, etc., as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed, and not a slurry, at the time of mixing.

For example, when a mixed metal oxide of the formula $Mo_a V_b Te_c Nb_x O_n$, wherein the element A is Mo, the element M is V, the element N is Te and the element X is Nb, is to be prepared, an aqueous solution of telluric acid, an aqueous solution of niobium oxalate and a solution or slurry of ammonium paramolybdate may be sequentially added to an aqueous solution containing a predetermined amount of ammonium metavanadate, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mmHg to 500 mmHg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally preferred.

Once obtained, the catalyst precursor is calcined. The calcination may be conducted in an oxidizing atmosphere, but it is also possible to conduct the calcination in a non-oxidizing atmosphere plus e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thercover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired mixed metal oxide.

In a preferred mode of operation, the catalyst precursor is calcined in two stages. In the first stage, the catalyst precursor is calcined in an oxidizing atmosphere (e.g., air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for from 15 minutes to 8 hours, preferably for from 1 to 3 hours. Optionally, a reducing gas, such as, for example, ammonia or hydrogen, may be added during the second stage calcination.

In a particularly preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

With calcination, a catalyst is formed having the formula $A_a M_m N_n X_x O_o$ wherein A, M, N, X, O, a, m, n, x and o are as previously defined.

The starting materials for the above mixed metal oxide are not limited to those described above. A wide range of materials including, for example, oxides, nitrates, halides or oxyhalides, alkoxides, acetylacetonates and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

A mixed metal oxide, thus obtained, exhibits excellent catalytic activities by itself. However, the mixed metal oxide can be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned mixed metal oxide, the viscosity, the concentration, etc. of the solvent used in the case of wet grinding, or the optimum conditions of the grinding apparatus. However, it is preferred that grinding is conducted until the average particle size of the ground catalyst precursor would usually be at most 20 μm, more preferably at most 5 μm. Improvement in the catalytic performance may be brought about by such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by the spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The mixed metal oxide thus obtained may be used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor.

Alternatively, the metal components of the presently contemplated catalyst may be supported on materials such as alumina, silica, silica-alumina, zirconia, titania, etc. by conventional incipient wetness techniques. In one typical method, solutions containing the metals are contacted with the dry support such thatbthe support is wetted; then, the resultant wetted material is dried, for example, at a temperature from room temperature to 200° C. followed by calcination as described above. In another method, metal solutions are contacted with the support, typically in volume ratios of greater than 3:1 (metal solution:support), and the solution agitated such that the metal ions are ion-exchanged onto the support. The metal containing support is then dried and calcined as detailed above.

Alternatively, other catalysts which can be utilized in the processes of the present invention include, for example, zeolites, metal-containing zeolites, superacids, polyoxometallates, solid bases, supported metals, aluminum phosphates, metal-substituted aluminum phosphates, mesoporous structures, etc.

In its first aspect, the method of the present invention comprises subjecting a mixture of an alkene and an alkane, to a single-pass vapor phase catalytic oxidation reaction in the presence of a catalyst containing a mixed metal oxide having the formula

wherein A is at least one element selected from the group consisting of molybdenum and tungsten, M is at least one element selected from the group consisting of vanadium and cerium, N is at least one element selected from the group consisting of tellurium and selenium, and X is at least one element selected from the group consisting of niobium, tantalum, titanium, aluminum, zirconium, chromium, manganese, iron, ruthenium, cobalt, rhodium, nickel, platinum, antimony, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium, and
wherein when a=1, m=0.01 to 1.0, n=0.01 to 1.0, x=0.01 to 1.0 and o is dependent on the oxidation state of the other elements; to produce an unsaturated carboxylic acid. By a single-pass vapor phase catalytic oxidation reaction is meant a vapor phase catalytic oxidation reaction wherein the reactants only pass through the reaction zone, i.e. over and/or through the catalyst bed, one time. There is no recycle of any unreacted reactants nor is there any recycle of reacted materials be they products or by-products of the reaction.

In the production of such an unsaturated carboxylic acid, it is preferred to employ a starting material gas which contains steam. In such a case, as a starting material gas to be supplied to the reaction system, a gas mixture comprising a steam-containing alkene, or a steam-containing mixture of alkene and alkane, and an oxygen-containing gas, is usually used. However, the steam-containing alkene, or the steam-containing mixture of alkene and alkane, and the oxygen-containing gas may be alternately supplied to the reaction system. The steam to be employed may be present in the form of steam gas in the reaction system, and the manner of its introduction is not particularly limited.

Further, as a diluting gas, there may be used carbon monoxide, carbon dioxide or mixtures thereof; an inert gas such as nitrogen, argon, helium or mixtures thereof; or mixtures thereof. The molar ratio (mixture of alkene and alkane):(oxygen):(diluting gas):($H_2O$) in the starting material gas is preferably (1):(0.1 to 10):(0 to 20):(0.2 to 70), more preferably (1):(1 to 5.0):(0 to 10):(5 to 40).

When steam is supplied together with the mixture of alkene and alkane, as starting material gas, the selectivity for an unsaturated carboxylic acid is distinctly improved, and the unsaturated carboxylic acid can be obtained from the mixture of alkene and alkane, in good yield simply by contacting in one stage. However, the conventional technique utilizes a diluting gas, as described above, for the purpose of diluting the starting material. Such a diluting gas is used to adjust the space velocity, the oxygen partial pressure and the steam partial pressure.

In the present invention, as the starting material mixture of alkene and alkane, it is preferred to employ a mixture of $C_{3-8}$ alkene and $C_{3-8}$ alkane, particularly propene and propane, isobutene and isobutane or n-butene and n-butane. As the starting material mixture of alkene and alkane, propene and propane or isobutene and isobutane are more preferred. Most preferred is a mixture of propene and propane. According to the present invention, from such a mixture of an alkene and an alkane, an unsaturated carboxylic acid such as an α,β-unsaturated carboxylic acid can be obtained in good yield. For example, when propene and propane or isobutene and isobutane are used as the starting material mixture of alkene and alkane, acrylic acid or methacrylic acid will be obtained, respectively, in good yield. In the mixture of alkene and alkane, the alkene is present in an amount of at least 0.5% by weight up to 95% by weight, preferably at least 0.5% by weight to 10% by weight; most preferably, 0.5% by weight to 5% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material mixture of alkene and alkane is not particularly limited, and a mixture of alkene and alkane containing a lower alkene such as ethene, a lower alkane such as methane or ethane, air or carbon dioxide, as impurities, may be used without any particular problem. Further, the starting material mixture of alkene and alkane may be a mixture of various alkenes and alkanes.

There is no limitation on the source of the alkene. It may be purchased, per se, or in admixture with an alkane and/or other impurities. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only a mixture of alkene and alkane substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

The first aspect of the present invention will be described in further detail with respect to a case where propene and propane are used as the starting material mixture of alkene and alkane and air is used as the oxygen source. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propene/propane mixture, whereby high selectivity for acrylic acid can be obtained. This reaction can be conducted usually under atmospheric pressure, but may be conducted under a slightly elevated pressure or slightly reduced pressure. With respect to other mixtures of alkene(s) and alkane (s), the composition of the feed gas may be selected in accordance with the conditions for the mixture of propene and propane.

Typical reaction conditions for the oxidation of propane or isobutane to acrylic or methacrylic acid may be utilized in the practice of the present invention. General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reactor is usually within a range of from 100 to 10,000 hr$^{-1}$, preferably 300 to 6,000 hr$^{-1}$, more preferably 300 to 2,000 hr$^{-1}$; the average contact time with the catalyst can be from 0.01 to 10 seconds or more, but is usually in the range of from 0.1 to 10 seconds, preferably from 2 to 6 seconds; the pressure in the reaction zone usually ranges from 0 to 75 psig, but is preferably no more than 50 psig.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen level be low to minimize after-burning. In addition, operation of the reaction at a low temperature (below 450° C.) is extremely attractive because after-burning becomes 14 ss of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propene and propane, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it to a vapor phase catalytic oxidation reaction with a conventional oxidation reaction catalyst for an unsaturated aldehyde.

In its second aspect, the method of the present invention comprises subjecting an alkene, or a mixture of an alkene and an alkane, containing at least 0.5% by weight of said alkene, to a vapor phase catalytic oxidation reaction with ammonia in the presence of a catalyst containing a mixed metal oxide having the formula

wherein A is at least one element selected from the group consisting of molybdenum and tungsten, M is at least one element selected from the group consisting of vanadium and cerium, N is at least one element selected from the group consisting of tellurium, antimony and selenium, and X is at least one element selected from the group consisting of niobium, tantalum, titanium, aluminum, zirconium, chromium, manganese, iron, ruthenium, cobalt, rhodium, nickel, platinum, antimony, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium; and wherein when a=1, m=0.01 to 1.0, n=0.01 to 1.0, x=0.01 to 1.0 and o is dependent on the oxidation state of the other elements, to produce an unsaturated nitrile.

In the production of such an unsaturated nitrile, as the starting material alkene, it is preferred to employ a $C_{3-8}$ alkene such as propene, butene, isobutene, pentene, hexene and heptene. However, in view of the industrial application of nitrites to be produced, it is preferred to employ a lower alkene having 3 or 4 carbon atoms, particularly propene and isobutene.

Similarly, as the starting material mixture of alkene and alkane, it is preferred to employ a mixture of $C_{3-8}$ alkene and $C_{3-8}$ alkane such as propene and propane, butene and butane, isobutene and isobutane, pentene and pentane, hexene and hexane, and heptene and heptane. However, in view of the industrial application of nitrites to be produced, it is more preferred to employ a mixture of a lower alkene having 3 or 4 carbon atoms and a lower alkane having 3 or 4 carbon atoms, particularly propene and propane or isobutene and isobutane. Preferably, in the mixture of alkene and alkane, the alkene is present in an amount of at least 0.5% by weight up to 95% by weight, preferably at least 0.5% by weight to 10% by weight, most preferably 0.5% by weight to 5% by weight.

The purity of the starting material alkene is not particularly limited, and an alkene containing a lower alkene such as ethene, air or carbon dioxide, as impurities, may be used without any particular problem. Further, the starting material alkene may be a mixture of various alkenes. Similarly, the purity of the starting material mixture of alkene and alkane is not particularly limited, and a mixture of alkene and alkane containing a lower alkene such as ethene, a lower alkane such as methane or ethane, air or carbon dioxide, as impurities, may be used without any particular problem. Further, the starting material mixture of alkene and alkane may be a mixture of various alkenes and alkanes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of this aspect of the present invention is not clearly understood. However, the oxidation reaction is conducted by the oxygen atoms present in the above mixed metal oxide or by the molecular oxygen in the feed gas. When molecular oxygen is incorporated in the feed gas, the oxygen may be pure oxygen gas. However, since high purity is not required, it is usually economical to use an oxygen containing gas such as air.

As the feed gas, it is possible to use a gas mixture comprising an alkene, or a mixture of an alkene and an alkane, ammonia and an oxygen-containing gas, However, a gas mixture comprising an alkene or a mixture of an alkene and an alkane and ammonia, and an oxygen-containing gas may be supplied alternately.

When the gas phase catalytic reaction is conducted using an alkene, or a mixture of an alkene and an alkane, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

The second aspect of the present invention will be described in further detail with respect to a case where propene is used as the starting material alkene and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propene. The proportion of ammonia to be supplied for the reaction is preferably within a range of from 0.2 to 5 moles, particularly from 0.5 to 3 moles, per mole of propene. This reaction may usually be conducted under atmospheric pressure, but may be conducted under a slightly increased pressure or a slightly reduced pressure. With respect to other alkenes such as isobutene, or to mixtures of alkenes and alkanes such as propene and propane, the composition of the feed gas may be selected in accordance with the conditions for propene.

The process of the second aspect of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 hr$^{-1}$, preferably from 300 to 6,000 hr$^{-1}$, more preferably from 300 to 2,000 hr$^{-1}$. As a diluent gas, for adjusting the space velocity and the oxygen partial pressure, there may be used carbon monoxide, carbon dioxide or mixtures thereof; an inert gas such as nitrogen, argon, helium or mixtures thereof; or mixtures thereof. When ammoxidation of propene is conducted by the method of the present invention, in addition to acrylonitrile, carbon monoxide, carbon dioxide, acetonitrile, hydrocyanic acid and acrolein may form as by-products.

The mixed metal oxide having the formula $A_aM_mN_nX_xO_o$, prepared in the manner as described above, has adequate catalytic activity by itself. However, in order to further improve the selectivity and yield of the nitrile, it is particularly preferred to use a catalyst having a certain specific oxide incorporated therein. As such a specific oxide, it is possible to employ an oxide containing at least one member selected from the group consisting of antimony, bismuth, cerium and boron. An antimony oxide is particularly preferred.

The antimony oxide may, for example, be an antimony oxide such as $Sb_2O_3$, $Sb_2O_4$ or $Sb_2O_5$, or it may be a complex antimony oxide, e.g., $SbO_2.(Sb_2O_4)$. These oxides may be used alone or in combination as a mixture of a plurality of them. Alternatively, the oxide may be used in the form of a hydrate. Further, in some cases, it is possible to employ as a solid catalyst a substance prepared by incorporating an organic compound containing antimony, such as ammonium antimony tartarate or antimony oxalate, in the mixed metal oxide, followed by calcination. In this case, the organic compound containing antimony will be converted to antimony oxide by the calcination.

The bismuth oxide to be incorporated may, for example, be a bismuth oxide such as $Bi_2O_3$ or $Bi_2O_4$, and it may also be a hydrate such as $Bi_2O_4 \cdot 2H_2O$. These oxides may be used alone or in combination as a mixture of a plurality of them. In some cases, a salt of an organic or inorganic acid or a hydroxide containing bismuth, such as bismuth hydroxide, bismuth nitrate, bismuth nitrate oxide or bismuth acetate, may be added to the mixed metal oxide, followed by calcination, and the substance thereby obtained can be used as a solid catalyst. In this case, the salt or the hydroxide containg bismuth will be converted to bismuth oxide by the calcination.

The cerium oxide may, for example, be a cerium oxide such as $Ce_2O_3$ or $CeO_2$. These oxides may be used alone or in combination as a mixture of a plurality of them. In some cases, a salt of an organic or inorganic acid or a hydroxide containing cerium, such as cerium nitrate, cerium hydroxide, cerium oxalate or cerium acetate, may be added to the mixed metal oxide, followed by calcination, and the product of the calcination can be used as a solid catalyst. In this case, the salt or the hydroxide containing cerium will be converted to cerium oxide by the calcination.

The boron oxide is usually $B_2O_3$. However, a boric acid or a boric acid ester, such as orthoboric acid, metaboric acid, ethyl borate or propyl borate, may be added to the mixed metal oxide, followed by calcination, and the calcined product can be used as a solid catalyst. In such a case, the boric acid or the the boric acis ester is believed to be converted to boron oxide by the calcination.

As a method for incorporating the above-mentioned specific oxides into the mixed metal oxide, it is advisable to pulverize and mix both materials so that the contact of the specific oxide with the mixed metal oxide can be effectively done. The weight ratio of the specific oxide to the mixed metal oxide is usually from 0.0001 to 0.2, preferably from 0.001 to 0.05. After the addition, the mixture may be used as it is for the reaction to produce a nitrile. However, in order to effectively obtain the benfit of the addition of the specific oxide, it is preferred to calcine the mixture again at a temperature of from 300° C. to 650° C., preferably from 350° C. to 600° C., usually for from 0.5 to 30 hours, preferably from 1 to 10 hours. The atmosphere for the calcination is not particularly limited, but it is usually preferred to employ an inert gas atmosphere such as nitrogen, argon or helium, and the inert gas may further contain a reducing gas such as hydrogen, ammonia or a hydrocarbon, or steam. Otherwise, the calcination may be conducted under vacuum.

Even if the specific oxide is added to the mixed metal oxide, followed by mixing and calcination, the X-ray diffraction pattern of the obtained product is substantially the same as that of the mixed metal oxide before the addition of the specific oxide, and there is no substantial change observed in the crystal structure.

The so-formed catalyst may be used alone, however, it may also be used together with a conventional carrier such as silica, alumina, titania, aluminosilicate or diatomaceous earth. Further, depending upon the scale or system of the reaction, it may be molded into a proper shape and/or particle size.

EXAMPLES

Conversion of a mixed feed of propene and propane to acrylic acid, by oxidation with air in the presence of steam (total hydrocarbon in feed=7% by volume) over a mixed metal oxide catalyst, prepared in accord with the present invention, and containing Mo, V, Te and Nb as essential components, was effected at various temperatures and feed compositions with a residence time of 3 seconds. The results are shown in Table 1.

TABLE 1

| % $C_3H_8$ in $C_3$ Feed | % $C_3H_6$ in $C_3$ Feed | Temp. (° C.) | $C_3$ Converted (%) | Acrylic Acid Select. (%) | Acrylic Acid Yield (%) | $C_3H_6$ in HC product (%) |
|---|---|---|---|---|---|---|
| 100 | 0 | 370 | 51.7 | 60.8 | 31.4 | 2.9 |
| 95 | 5 | 370 | 54.3 | 59.2 | 32.1 | 1.2 |
| 90 | 10 | 370 | 54.0 | 54.8 | 29.6 | 1.1 |
| 80 | 20 | 350 | 49.8 | 35.6 | 17.7 | 0.7 |
| 50 | 50 | 340 | 50.3 | 42.8 | 21.5 | 0.0 |
| 50 | 50 | 355 | 56.0 | 43.1 | 24.1 | 0.0 |

In the above examples, the following definitions apply:
Conversion (%) = (moles of consumed $C_3$ component/moles of supplied $C_3$ component) × 100;
Selectivity (%) = (moles of formed acrylic acid product/moles of consumed $C_3$ component) × 100; and
Yield (%) = (moles of formed acrylic acid product/moles of supplied $C_3$ component) × 100.

What is claimed is:

1. A method for producing an unsaturated carboxylic acid, which comprises subjecting a mixture of an alkene and an alkane to a single-pass vapor phase catalytic oxidation reaction in the presence of a catalyst containing a mixed metal oxide having the formula $A_aM_mN_nX_xO_o$ wherein A is at least one element selected from the group consisting of molybdenum and tungsten, M is at least one element selected from the group consisting of vanadium and cerium, N is at least one element selected from the group consisting of tellurium and selenium, and X is at least one element selected from the group consisting of niobium, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium; and wherein when a=1, m=0.01 to 1.0, n=0.01 to 1.0, x=0.01 to 1.0 and o is dependent on the oxidation state of the other elements.

2. The method according to claim 1, wherein as a starting material gas to be supplied to the reaction system, steam is used together with the mixture of alkene and alkane.

3. The method according to claim 2, wherein as starting material gases to be supplied to the reaction system, oxygen and a diluting gas are used together with the mixture of an alkene and an alkane and steam; and wherein the molar ratio of the mixture of (alkene and alkane):(oxygen):(diluting gas):(steam) in the starting material gas is (1):(0.1 to 10):(0 to 20):(0.2 to 70).

4. The method according to claim 1, wherein the mixed metal oxide exhibits X-ray diffraction peaks at the following diffraction angles 2θ in the X-ray diffraction pattern using Cu—Kα radiation:

Diffraction angle 2θ (±0.3°)
22.1°,
28.2°,
36.2°,
45.2°,
50.0°.

5. The method according to claim 1, wherein M is vanadium.

6. The method according to claim 5, wherein N is tellurium.

7. The method according to claim 6, wherein X is niobium.

8. The method according to claim 1, wherein the alkene is propene and the alkane is propane.

9. The method according to claim 8, wherein the alkene is present in an amount of at least 0.5% by weight up to 10% by weight.

* * * * *